(12) United States Patent
Dao et al.

(10) Patent No.: US 8,753,664 B2
(45) Date of Patent: Jun. 17, 2014

(54) MEDICAL DEVICE INTENDED TO COME INTO CONTACT WITH A PATIENT'S TISSUE AND RELATED MANUFACTURING METHOD

(75) Inventors: Vithuy Dao, Fresnes (FR); Robert Michelot, Antony (FR); Eric Perouse, Paris (FR)

(73) Assignee: Perouse Medical, Ivry Le Temple (FR)

( * ) Notice: Subject to any disclaimer, the term of this patent is extended or adjusted under 35 U.S.C. 154(b) by 0 days.

(21) Appl. No.: 13/316,022

(22) Filed: Dec. 9, 2011

(65) Prior Publication Data

US 2012/0177719 A1    Jul. 12, 2012

(30) Foreign Application Priority Data

Dec. 13, 2010 (FR) ...................................... 10 60414

(51) Int. Cl.
- *A61F 2/00* (2006.01)
- *A61K 8/73* (2006.01)
- *A61K 9/70* (2006.01)

(52) U.S. Cl.
CPC ............... *A61K 8/731* (2013.01); *A61K 9/7007* (2013.01)
USPC ......................................... 424/423; 424/426

(58) Field of Classification Search
CPC ............................... A61K 8/731; A61K 9/7007
USPC .................................................. 424/423, 426
See application file for complete search history.

(56) References Cited

U.S. PATENT DOCUMENTS

| 2,423,707 | A | * | 7/1947 | Kenyon et al. ............ 139/426 R |
| 6,921,819 | B2 | | 7/2005 | Prion et al. |
| 2005/0208095 | A1 | * | 9/2005 | Hunter et al. ................. 424/423 |
| 2009/0156711 | A1 | | 6/2009 | Van Holten |
| 2010/0184968 | A1 | | 7/2010 | Bertholon et al. |
| 2011/0264237 | A1 | | 10/2011 | Bayon et al. |

FOREIGN PATENT DOCUMENTS

| EP | 0492990 | 9/1995 |
| FR | 2 742 042 | 6/1997 |
| FR | 2 937 244 | 4/2010 |
| WO | WO 2006/044881 | 4/2006 |
| WO | WO 2009/016325 | 2/2009 |

OTHER PUBLICATIONS

Hacker et al., "Synthetic Polymers," Principles of Regenerative Medicine, $2^{nd}$ edition, 2011, Elsevier, Chapter 33, see pp. 590 to 596.

* cited by examiner

*Primary Examiner* — Benjamin Packard
(74) *Attorney, Agent, or Firm* — Davidson, Davidson & Kappel, LLC

(57) ABSTRACT

A device including a body (12) including fibers without oxidized cellulose. The body (12) also includes fibers containing oxidized cellulose.

16 Claims, 3 Drawing Sheets

MEDICAL DEVICE INTENDED TO COME INTO CONTACT WITH A PATIENT'S TISSUE AND RELATED MANUFACTURING METHOD

This claims the benefit of French Patent Application FR 10 604 14, filed Dec. 13, 2010 and hereby incorporated by reference herein.

The present invention relates to a medical device intended to come into contact with a patient's tissue, comprising a body having fibers provided without oxidized cellulose.

BACKGROUND

Such a medical device is intended for example to form a prosthesis or a vascular endoprosthesis, a guided tissue regeneration membrane, a tube, a setting plate, a dialysis catheter, a perfusion catheter, a transfusion catheter, an artificial alimentation catheter, a transcutaneous implant, a lattice for tissue engineering, a micro and macro porous bone substitute, a dura mater substitute, a cell therapy matrix, a suture thread, a medical bandage or a vascular patch.

Known from FR 2 742 042 is a medical device of the aforementioned type forming a tubular vascular prosthesis.

Vascular prostheses are generally made from a tissue or a tightly-knit fabric. Before they are implanted, they are coated with a coating that ensures both the biocompatibility and sealing of the device.

This coating is for example formed with a base of collagen, gelatin or another composition comprising a bioresorptive polymer.

The vascular prosthesis, once implanted in the body, is intended to convey blood to replace an obstructed or destroyed blood vessel.

To that end, the coating layer guarantees the sealing of the prosthesis once it is implanted, before the cells colonize the walls of the textile substrate to maintain sealing.

To that end, when the surgeon reestablishes the blood pressure after having sewn the prosthesis, the collagen coating prevents the blood from passing and seeping through the mesh of the prosthesis knit, so that the patient does not lose too much blood.

Such prostheses are completely satisfactory, in particular regarding sealing.

Nevertheless, it may be useful in some cases to do away with coatings of animal origin, while keeping good sealing and good mechanical properties.

SUMMARY OF THE INVENTION

It is an object of the present invention to provide a medical device, in particular a vascular prosthesis, that has a suitable mechanical structure, while preserving satisfactory sealing and hemostatic properties.

The present invention provides a medical device of the aforementioned type, characterized in that the body includes fibers containing oxidized cellulose.

The device according to the invention can include one or more of the following features, considered alone or according to all technically possible combinations:
- at least part of the fibers provided without oxidized cellulose is assembled with the fibers containing oxidized cellulose to form at least one composite thread, the composite thread being braided, woven or knitted, to form the body;
- the fibers containing oxidized cellulose form at least one first thread, the fibers without oxidized cellulose forming at least one second thread, the first and second threads being braided, woven or knitted to form the body;
- the body is a non-woven;
- the fibers of the non-woven body are oriented in a preferred direction;
- the fibers without oxidized cellulose are chosen from among synthetic polymers and natural polymers provided without oxidized cellulose;
- the fibers without oxidized cellulose are formed from a polymer from the group made up of polyamides, polyolefins, halogenated polymers, polyesters, polyurethanes, fluorinated polymers, polylactic or polyglycidyl acids or mixtures thereof;
- the oxidized cellulose contained in the fibers containing oxidized cellulose is functionalized by a functional group;
- the oxidized cellulose includes a carboxyl group supported by the carbon 6 of the anhydroglucose unit, the carboxyl group being functionalized by the functional group;
- the functional group is chosen from among a bioreactive agent such as an anticoagulant, an antithrombogenic, an antimitotic, an anti-proliferation agent, an anti-adhesion agent, an anti-migration agent, a cell adhesion promoter, a growth factor, an anti-parasite molecule, an anti-inflammatory, an angiogenic, an angiogenesis inhibiter, a vitamin, a hormone, a protein, an antifungal, an antimicrobial molecule, an antiseptic, a cross-linking agent, a contrast agent;
- the body forms a tube or sheet;
- the body delimits a liquid-tight wall, advantageously sealed against blood;
- the device forms a prosthesis or a vascular endoprosthesis, a guided tissue regeneration membrane, a tube, a setting plate, a dialysis catheter, a perfusion catheter, a transfusion catheter, an artificial alimentation catheter, a transcutaneous implant, a lattice for tissue engineering, a micro and macro porous bone substitute, a dura mater substitute, a cell therapy matrix, a suture thread, a medical bandage or a vascular patch.

The invention also relates to a method of manufacturing a medical device intended to come into contact with a patient's tissue, characterized in that it includes a step for producing a body including fibers without oxidized cellulose and fibers comprising oxidized cellulose.

The method according to the invention can comprise one or more of the following features, considered alone or according to all technically possible combinations:
- it includes the following steps:
  providing fibers without oxidized cellulose and fibers comprising cellulose intended to be oxidized;
  forming the body from fibers provided without oxidized cellulose and cellulose fibers intended to be oxidized;
  selective oxidation of the cellulose fibers intended to be oxidized, after formation of the body to form the oxidized cellulose;
- it comprises, before the formation of the body, the assembly of at least one composite thread including fibers without oxidized cellulose and cellulose fibers intended to be oxidized, and braiding, knitting or weaving the composite thread to form the body;
- the formation of the body includes the provision of at least one first thread formed from fibers without oxidized cellulose and at least one second thread formed from cellulose fibers intended to be oxidized, then braiding, weaving or knitting the first thread with the second thread to form the body;

it includes, after the oxidation step, at least partial functionalization of the cellulose oxidized by a functional group.

BRIEF DESCRIPTION OF THE DRAWINGS

The invention will be better understood upon reading the following description, provided solely as an example, and done in reference to the appended drawings, in which.

DETAILED DESCRIPTION

Figure 1:
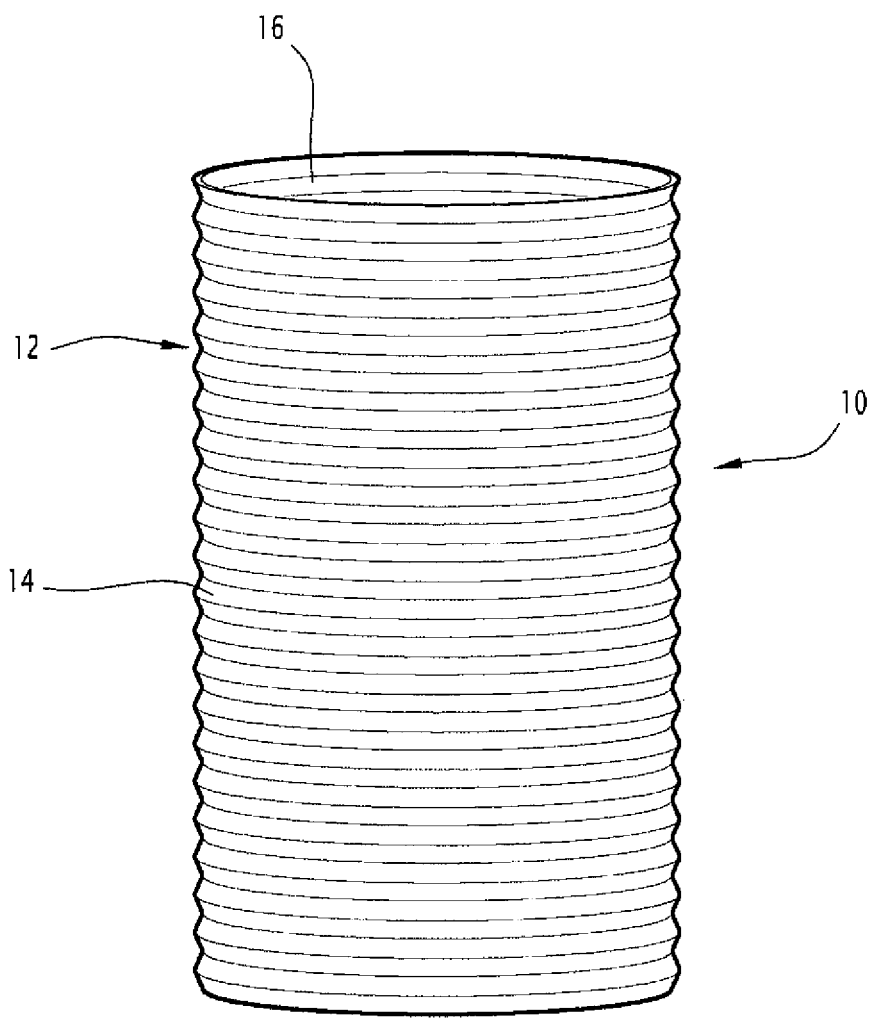
FIG. 1 is a side view of a first medical device according to the invention forming a vascular prosthesis.

A first medical device 10 according to the invention is shown in FIG. 1.

According to the invention, the first medical device 10 comprises a body 12 including fibers without oxidized cellulose and fibers containing oxidized cellulose.

In this example, the body 12 is for example formed from a fabric made with a base of woven, braided or knitted threads. In an alternative that will be described later, the body 12 is a nonwoven made by assembling fibers connected to one another.

The body 12 is a macroscopic body, i.e. having at least one dimension larger than 5 mm, preferably at least equal to 1 cm.

The fibers containing oxidized cellulose are obtained from cellulose fibers with general formula $-(C_6H_{10}O_5)n$-. In a known manner, the cellulose is a homopolymer belonging to the class of polysaccharides. It is formed from a linear chain of glucose molecules connected by glycosidic linkages β-1,4.

"Oxidized cellulose" refers, within the meaning of the present invention, to a cellulose in which at least part of the primary alcohol groups supported by the carbon 6 of the anhydroglucose unit is oxidized in a carboxylic acid that may be functionalized, as will be seen later.

The degree of oxidation of the oxidized cellulose is greater than 1%. Preferably, this degree of oxidation is between 1% and 25%, preferably from 5% to 20% and advantageously from 12% to 18%.

In the context of this description, "degree of oxidation" of a partially oxidized polymer-based material refers to the mass of the carboxylic acid groups contained in 100 g of said material, in percentage.

The degree of oxidation can be determined by titrimetry, according to the calcium exchange method (Sobue and Okubo, 1956), recommended by the United States Pharmacopeia (USP, 1990), according to the following protocol:

In a 250 mL Erlenmeyer flask, introduce 0.10 g of the partially oxidized cellulose tissue to be analyzed, add 50 mL of purified water and 30 mL of a calcium acetate solution at 0.5 N. Agitate the mixture on an orbital mixer for 3 hours.

Withdraw 30 mL of the sample and titrate with an aqueous solution of NaOH (0.01 N) in the presence of phenolphthalein. The volume of NaOH consumed is corrected by comparing that volume with a control sample not containing oxidized cellulose.

The corresponding equivalent quantity of carboxylic acid function is related to the degree of oxidation. The degree of oxidation, expressed in %, is calculated using the following formula:

$$\text{Degree of oxidation (\%)} = \frac{8}{3} \frac{V \times N \times M_{COOH}}{m_{tissu}} \times 100$$

where:

N (mol/L) is the normality of the NaOH solution (here N=0.01 mol/L),

V (L) is the volume of NaOH solution consumed to titrate the sample, $M_{COOH}$ (g/mol) is the molar mass of a carboxylic acid function ($M_{COOH}$=45 g/mol), $m_{tissu}$ (g) is the mass of the analyzed partially oxidized cellulose tissue (m=0.10 g).

The term "fiber" is understood as a filamentous elementary formation assuming the form of a bundle. A fiber differs from a foam in particular in that it has a length larger than its width, advantageously a length larger than 10 times its width.

In the context of this description, "linked fiber-based material" or "fibrous material" refers to a solid material comprising a set of fibers bound together, for example in the form of a thread, or in the form of a fabric made up of woven or knitted threads, for example, or in a nonwoven form, or in the form of a ply of fibers forming an oriented matrix.

In the context of this description, "thread" refers to a linear assembly of fibers or fibrils connected to one another securely. A cellulose thread must therefore be distinguished from a cellulose fiber, which designates an individual object and not a linked assembly of objects. Typically, a thread is obtained by spinning fibers of the same type, but can also be obtained by spinning different fibers, such as, for example, cellulose fibers combined with synthetic fibers.

The polymer making up the cellulose fibers comprises anhydroglucose units. It may for example involve cellulose fibers, i.e. made up of a glucose homopolymer with glycosidic linkages β-1,4. Alternatively, it may involve modified cellulose, on the condition that it includes anhydroglucose units, potentially connected with other units, for example viscose that corresponds to a thread obtained from regenerated cellulose. Alternatively, it may involve bacterial cellulose. Before oxidation of the fibers, the degree of oxidation of the polymer making up the fibers is generally less than 1%.

The cellulose fibers are for example obtained with a natural cellulose base, i.e. fibers coming directly from a plant, either by being harvested on the plant, or by being obtained through mechanical processing of the plant, such as shredding, pressing, crushing and/or separation. The cellulose fibers are also modified cellulose fibers, i.e. natural cellulose or solubilized natural cellulose, having reacted with a chemical component.

The term "cellulose fibers" also includes, within the meaning of the present invention, the regenerated cellulose fibers, i.e. natural cellulose, potentially modified, solubilized in a solvent, then reformed in the form of fibers.

The fibers containing cellulose contain at least 1% in moles, for example more than 50% in moles, of cellulose or a cellulose derivative.

Examples of natural plant cellulose fibers are cotton, hemp, jute, wool, or wood pulp.

Artificial cellulose fibers are obtained using a method for processing the natural cellulose.

These fibers are for example defined generically by the International Bureau for the Standardization of Man-made Fibers (BISFA) as being cellulose fibers of the "acetate" or "tri-acetate" type obtained through acetylation of the hydroxyl groups of the cellulose, fibers of the "alginate" type obtained from metallic salts of alginic acid, such as for example the alkaline or alkaline earth salts of alginic acid, such as calcium alginate, or "cupro"-type cellulose-based fibers obtained using the "cuprammonium" method, in which the natural cellulose is dissolved in a compound comprising copper and an amine such as cupratetratamine dihydroxide.

Advantageously, the cellulose fibers are viscose fibers.

"Viscose fiber" refers, within the meaning of the present invention, to fibers obtained using the "viscose" method according to the BISFA definition, wherein advantageously a basic solution of cellulose xanthate is drawn in the form of fibers from one or more regeneration baths. These fibers sometimes have a great resistance to breakage, however, and are then qualified as "modal."

In certain cases, and alternatively, the cellulose fibers are lyocell fibers. "Lyocell fiber" refers to cellulose fibers obtained using a spinning method from an organic solvent that comprises a mixture of organic chemical products and water, the term "spinning by solvent" referring to the dissolution of the cellulose in the solvent without the formation of a byproduct of the cellulose.

In this method qualified as "lyocell" by the BISFA, natural cellulose is for example dissolved in a mixture of water and an amine N-oxide, for example a tertiary amine-N-oxide such as N-methylmorpholine N-oxide, and is extruded through an air passage in a precipitating bath to form fibers.

"Fibers without oxidized cellulose" refers, within the meaning of this invention, to fibers without cellulose, such as synthetic fibers or fibers comprising cellulose, but whereof the degree of oxidation is less than 1%.

"Synthetic fibers" refers to fibers that have no natural precursor polymer, such as the fibers obtained by polymerization of a synthetic monomer, for example oil byproduct.

Synthetic fibers in particular comprise the polyamides, such as nylons, polyesters such as ethylene polyterephthalates, polyacrylates, polyurethanes, polylactic and polyglycolic acids, polyethylene glycols, poly($\alpha$-olefins) of the polyethylene type and halogenated polymers such as poly (halogeno-$\alpha$-olefins) such as polytetrafluoroethylene (PTFE) marketed under the name TEFLON® or polyvinylidene fluoride, their copolymers or the combination of those polymers.

Advantageously, the fibers are ethylene polyterephthalate fibers or polytetrafluoroethylene (PTFE) fibers.

In a first embodiment of the invention, the fibers without oxidized cellulose and the fibers comprising oxidized cellulose or cellulose intended to be oxidized are assembled together to form a composite thread, for example through a beaming method.

The composite thread is woven, braided or knitted alone or with another composite thread, or with a thread without fibers comprising oxidized cellulose, such as a thread made with a base of synthetic polymer as defined above, such as for example a PET or PTFE thread.

The threads formed from oxidized cellulose fibers for example have a titer between 20 dtex and 200 dtex, in particular comprised between 40 dtex and 160 dtex. This titer is for example comprised between 50 dtex and 150 dtex for the knit prostheses and between 100 and 150 dtex for the woven prostheses.

In one advantageous example, the composite thread includes oxidized cellulose fibers and PET or PTFE fibers assembled together.

The oxidation of the cellulose is thus done either before or after production of the composite thread.

In a second embodiment of the invention, the body 12 is made with a base of at least one first thread formed exclusively from fibers containing oxidized cellulose or cellulose intended to be oxidized and with a base of at least one second thread formed exclusively from fibers without oxidized cellulose.

The first and second threads are advantageously braided, woven or knitted to form the body 12.

The oxidation of the cellulose is thus done either before or after the production of the body 12.

In one advantageous example, the second thread is a PET or PTFE thread.

According to one advantageous alternative of the invention, the partially oxidized cellulose is functionalized by a functional group.

The oxidation step makes it possible to functionalize the polymer for grafting, chemically, of various radicals that may modify the interaction of the oxidized fibrous material with its biological environment.

In one embodiment, a functional group is bonded or replaces the hydroxyl group of the carboxylic acid function of the partially oxidized polymer, so that the partially oxidized cellulose is functionalized by bonding or addition of a functional group on the carboxylic acid functions present on the carbon 6 of the anhydroglucose unit.

This functional group is advantageously chosen from among an anticoagulant, an antithrombogenic, an antimitotic, an anti-proliferation agent, an anti-adhesion agent, an anti-migration agent, a cell adhesion promoter, a growth factor, an anti-parasite molecule, an anti-inflammatory, an angiogenic, an angiogenesis inhibiter, a vitamin, a hormone, a protein, an antifungal, an antimicrobial molecule, an antiseptic, a cross-linking agent, a contrast agent. The functional groups are for example chosen from among those described above.

The functional group is for example grafted on the carboxylic acid function by forming a covalent bond between one of the oxygen atoms of the carboxylic acid group and an electrophilic radical containing said functional group or its precursor. For example, by forming an ester —COO(R) function where R is the functional group, or by forming an amide —CO—NR1R2 function where R1 and/or R2 is (are) a functional group.

The carboxylic acid groups of the oxidized cellulose are typically activated before functionalization, by using a coupling agent and/or a coupling auxiliary.

Examples of coupling agents are hydrosoluble carbodiimides such as 1-ethyl-3-(3-dimethylaminopropyl) carbodiimide (EDC), 1-ethyl-3-(3-trimethylaminopropyl) carbodiimide (ETC) and 1-cyclohexyl-3-(2-morpholinoethyl) carbodiimide (CMC) as well as their salts and mixtures. In the context of the present invention, the use of EDC is preferred.

Examples of coupling auxiliaries are N-hydroxy succinimide (NHS), N-hydroxy benzotriazole (HOBt), 3,4-dihydro-3-hydroxy-4-oxo-1,2,3-benzotriazole (HOOBt), 1-hydroxy-7-azabenzotriazole (HAt) and N-hydroxysulfosuccinimide (sulfo NHS) and mixtures thereof. Without being limited to the choice of NHS, this is preferable for use in the present invention.

When the functional group is a cross-linking agent, it is bonded to at least two distinct carboxylic acid functions of the partially oxidized polymer or to hydroxyl functions which are available on the partially oxidized polymer.

Examples of cross-linking agents are given in U.S. Pat. No. 6,921,819, and can for example be chosen from among a polyamine or an aliphatic diamine in the presence of an activating reagent such as EDC, or a diglycidyl ether such as bis-phenol diglycidyl ether, 1,4-butanediol diglycidyl ether (BDDE), 1,2-bis(2,3-epoxypropoxy)ethylene or 1-(2,3-epoxypropyl)-2,3-epoxycyclohexane.

The level of cross-linking agent makes it possible to control the resorption of the fibers comprising partially oxidized cellulose in the case where the material is implanted in the body of a patent and in contact with the patient's tissues.

Examples of contrast agents are chelate complexes of gadolinium or iron oxide-based superparamagnetic nanoparticles.

"Contrast agent" refers to an agent that may appear visible, with a contrast relative to the rest of the medical device on an image of the device done through the patient's skin, in particular by radiography, or by nuclear magnetic resonance.

Alternatively, the functional group is physically bonded to the carboxylic group of the partially oxidized polymer, for example by ion bond when the functional group is bonded to a polyamine.

The body 12 formed from fibers containing oxidized cellulose and fibers without oxidized cellulose forms a wall 14 sealed against bodily fluids such as blood, advantageously in the absence of an additional sealing coating.

Thus, the wall 14 is hemostatic, i.e. it prevents the passage of blood when the prosthesis is implanted, in particular through the so-called "clotting" effect or coagulation when the blood comes into contact with the oxidized cellulose.

The sealing of the body 12 against blood is for example determined by standard ISO 7198.

Furthermore, the fibers containing oxidized cellulose are resorptive, once implanted in a patient's body, which favors repopulation by fibroblasts, or even cellular regeneration of an organ.

In the example illustrated in FIG. 1, the body 12 of the device 10 is a tube including a substantially cylindrical wall 14.

In one alternative, the body 12 has a cylindrical primary section and two bifurcations generally in the shape of a Y.

The body 12 inwardly delimits a conduit 16 for circulation of the blood emerging at the ends of the wall 14.

The wall 14 prevents the passage of blood from the conduit 16 toward the outside by the presence of fibers containing oxidized cellulose and fibers without oxidized cellulose, in particular in the absence of a sealing coating.

Figure 2:
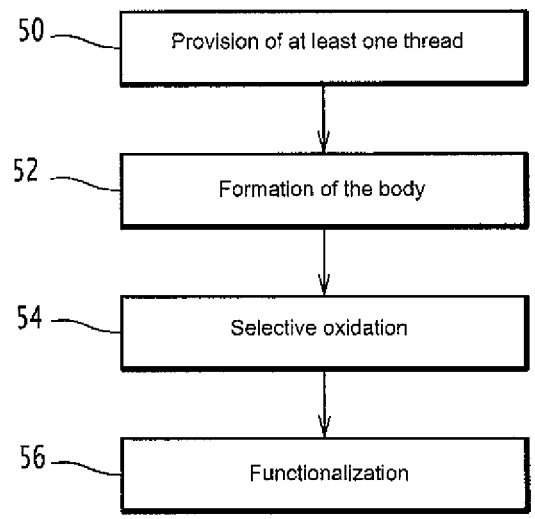
FIG. 2 is a functional overview diagram illustrating the different steps of a method for manufacturing a medical device according to the invention.

A method for manufacturing a medical device 10 according to the invention is shown diagrammatically in FIG. 2.

This method comprises an initial step 50 for providing at least one thread including cellulose intended to be oxidized, then a step for producing the body 12, and then a step 54 for selective oxidation of the cellulose intended to be oxidized.

The method also includes an optional step 56 for functionalization of the oxidized cellulose.

In the supply step 50, and in the first embodiment described above, at least one thread is made from cellulose fibers intended to be oxidized, and fibers without oxidized cellulose, such as synthetic fibers.

These fibers are assembled together to form a continuous thread, for example by beaming.

In the second embodiment, at least one first thread is formed with a base of fibers comprising cellulose intended to be oxidized and at least one second thread is formed from fibers without oxidized cellulose, such as synthetic fibers.

Then, in step 52, the body 12 is made by interlacing the or each thread, for example by weaving, braiding, or knitting to form the wall 14 comprising meshes. The fibers containing cellulose intended to be oxidized not comprising a significant quantity of oxidized cellulose, they are particularly robust. They can easily be woven, braided or knitted while limiting the risk of breakage.

The cellulose fibers intended to be oxidized have a degree of oxidation advantageously below 1%. They are preferably natural or synthetic cellulose fibers, or synthetic fibers or other natural fibers possibly containing cellulose, but without oxidized cellulose, not having received a particular oxidizing chemical treatment.

In one favored embodiment, the threads are shaped in the form of a fabric by knitting. Different meshes can be considered, in particular jersey (traditionally knit with a thread of 220 dtex with 42 filaments) or crochet (advantageously knitted with the thread 110 dtex with 40 filaments).

Typically, the fabric has a grammage in the vicinity of 50 $g/m^2$ to 100 $g/m^2$.

Then, in step 54, a selective oxidation of the cellulose intended to be oxidized is done, without significant oxidation of the fibers provided without oxidized cellulose.

This selective oxidation is done for example using a method of submitting the cellulose intended to be oxidized to the action of a nitrogen oxide such as $NO_2$ in the presence of solvents. Such a method for example involves soaking the body in a bath of solvent with sparging of gaseous $NO_2$, as described for example in patent application EP 0 492 990.

Alternatively, the selective oxidation is done by oxidation of the oxidized cellulose present in the body 12 using a hypohalite, advantageously in the presence of an oxoammonium salt, as described in international patent application WO 2009/016325 by the company SYMATESE. Advantageously, the hypohalite and the sodium hypochlorite and the oxoammonium salt is a salt of 2,2,6,6-tetramethylpiperidine-1-oxide (Tempo).

In one preferred alternative, the cellulose is oxidized by putting it in contact with an oxidizing mixture comprising a hypohalite, a halite, and an oxoammonium salt or a precursor of said salt, which leads to obtaining a material with a base of linked fibers with a base of the partially oxidized polymer. Such a method is described in the French patent application by the Applicant filed under number 10 60 416.

The oxidation step does not modify the macroscopic structure of the fibrous material, but only its molecular structure. The individual cellulose fibers, i.e. fibers not secured to one another, are in particular excluded from the definition of the fibrous material processed according to the inventive method.

Once the oxidation operation is performed, the degree of oxidation of the oxidized cellulose fibers is greater than 1%, as measured using the method described above. Preferably, this degree of oxidation is comprised from 1% to 25%, preferably from 5% to 20% and advantageously from 12% to 18%.

Optionally, in step 56, the oxidized cellulose is functionalized by bonding or adding a functional group on the carboxylic acid functions present on the carbon 6 of the anhydroglucose unit.

The functional groups are for example chosen from among those described above. These groups are for example covalently bonded to the oxidized cellulose by replacing the hydroxyl function of the carboxylic acid as described above.

Alternatively, the functional group is bonded by ionic bonding, by interaction between the ionized carboxylic acid and an ion with a different polarity.

Once manufactured, the medical device is advantageously placed in contact with a patient's tissue, for example by being implanted in the patient's body.

In the example illustrated in FIG. 1, blood circulates in the conduit 16 delimited by the wall 14, without seeping through said wall 14 owing to the presence of the oxidized cellulose fibers.

Figure 3:
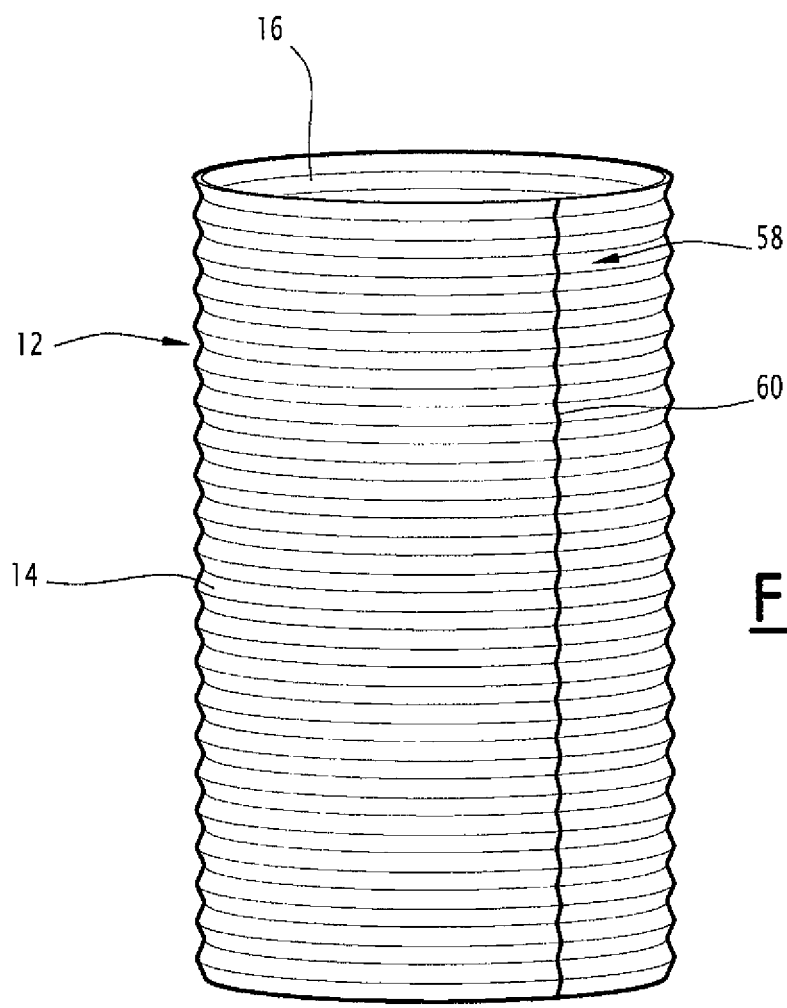
FIG. 3 is a figure similar to FIG. 1 of a second medical device according to the invention.

One alternative 58 of the device 10 is shown in FIG. 3. Unlike the device 10 shown in FIG. 1, the device 58 shown in FIG. 3 comprises a body 12 comprising a warp yarn 60 including oxidized cellulose functionalized by a contrast agent.

The warp yarn 60 extends for example along a generatrix of the wall 14. That yarn 60 is thus visible when an image is done through the patient's tissues, for example by radiography using X rays or by nuclear magnetic resonance.

Figure 4:
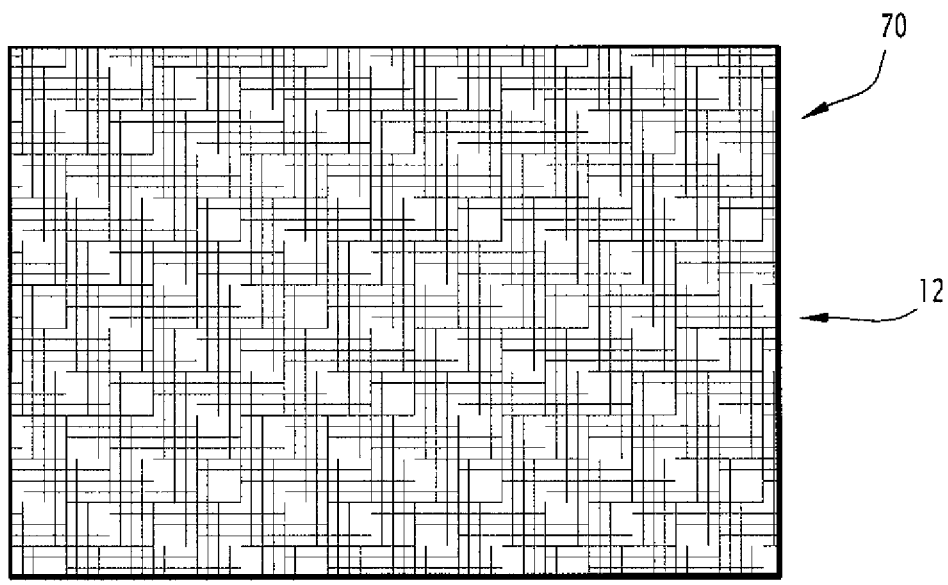
FIG. 4 is a view similar to FIG. 1 of a third device according to the invention for example forming a dressing gauze or a vascular patch.

A third medical device 70 according to the invention is shown in FIG. 4. Unlike the first device, this device includes a body 12 in the shape of a leaf having a thickness smaller than its maximum length and width.

The body 12 is advantageously deformable to the touch. This body 12 is for example a dressing gauze or a vascular patch.

In one alternative, the body 12 is a nonwoven. "Nonwoven" refers, within the meaning of the present invention, to a substrate comprising fibers without oxidized cellulose and fibers comprising oxidized cellulose in which the individual fibers or the filaments are positioned in a disordered manner in a structure in the form of a ply and that are neither woven nor knitted. The fibers of the nonwoven body are generally connected to one another, either under the effect of a mechanical action, such as a jet of water, for example, or under the effect of a thermal action, or by adding a binder.

Such a "nonwoven" is for example defined in standard ISO 9092 as a fiber web or ply oriented directionally or randomly, bonded by friction and/or cohesion and/or adhesion, to the exclusion of paper and products obtained by weaving, knitting, tufting or sewing.

The nonwoven body within the meaning of the present invention is for example obtained using a dry method, in particular by carding, or using an aerodynamic method referred to using the term "air laid." Alternatively, the nonwoven body according to the invention is obtained using a wet method in a method similar to that for obtaining a paper.

In one alternative, the fibers intended to form the nonwoven body are oriented in a preferred direction before the fibers are bound to each other. This preferred orientation is kept in the body 12 after binding the fibers. This orientation of the fibers favors cell colonization, once the body 12 is implanted in the patient.

The preferred orientation of the fibers is obtained for example by subjecting the fibers to an electrostatic field according to a method referred to as "electrospinning."

In other alternatives, the device forms a vascular endoprosthesis, a guided tissue regeneration membrane, a tube, a setting plate, a dialysis catheter, a perfusion catheter, a transfusion catheter, an artificial alimentation catheter, a transcutaneous implant, a lattice for tissue engineering, a micro and macro porous bone substitute, a dura mater substitute, a cell therapy matrix, a suture thread, a medical bandage or a vascular patch.

In a variation, a spacer group is inserted between the functional group and the carboxyl group of the oxidized cellulose. The spacer group is advantageously labile and can selectively be cleaved.

As it results directly and unambiguously from the preceding description, the fibers containing oxydized cellulose are resorptive.

The resorptive nature of these fibers can be verified for example using a protocol which can be carried out according to the Standard NF-EN ISO 10993-6 dated December 2009.

Several trial specimens, defined according to paragraph B3 of the appendix B of the above mentioned Standard are prepared from the implant. Each specimen is weighed.

The total amount of cellulose which is contained in the specimens is measured for example by proportioning. Next, the initial degree of oxidation of the cellulose is determined by the above described method.

Then, several specimens are implanted according to the methods which are disclosed in paragraph 5 of the above mentioned Standard, for example in a rat.

Subsequently, the implanted specimens are recovered, after a trial time such as defined in the Standard, for example, equal to 52 weeks.

The weight loss of each specimen is measured. The total amount of cellulose available in the specimens, as well as the degree of oxidation of the cellulose are measured as described above. A loss of weight, in combination with a decrease of the total amount of cellulose and a decrease of the degree of oxidation of the cellulose, indicates that the oxidized cellulose which is initially available in the implant is at least partially resorptive.

On the contrary, the non resorptive fibers have a mass variation which is lower than 10% of their initial mass when they are implanted according to the above defined protocol.

As shown above, non resorptive fibers without oxidized cellulose are advantageously chosen among the polyamides, such as nylons, polyterephthalates, polyacrylates, hydraulically stable polyurethanes, polyethylene glycols, poly($\alpha$-olefins) of the polyethylene type and halogenated polymers such as poly(halogeno-$\alpha$-olefins) such as polytetrafluoroethylene (PTFE) marketed under the name TEFLON® or polyvinylidene fluoride, their copolymers or the combination of those polymers.

More generally, the non resorptive fibers without oxidized cellulose are formed from synthetic polymers and copolymers which are non-biodegradable, such as disclosed in the book "Principles of Regenerative Medicine, $2^{nd}$ edition, 2011, Elsevier, Chapter 33, pages 590 to 596".

These polymers include polyethylene and derivatives, in particular polyethylene, polypropylene, polystyrene, halogenated polymers such as poly(tetrafluoroethylene), acrylic and methacrylic polymers and polyacylamides, such as poly(m-ethylmethacrylate), poly(2-hydroxyethylmethacrylate), poly(N-isopropylacrylamide), their copolymers or their mixtures, the poly(N-isopropylacrylamide) being advantageously used as a copolymer.

In a variation, the non resorptive fibers without oxidized cellulose are formed from polyethers such as PEEK, or from polyethyleneglycol, advantageously used as a copolymer. In a variation, the non resorptive fibers without oxidized cellulose are formed from polymers chosen among polysiloxanes or silicones such as poly(dimethylsiloxane) and their copolymers.

In another variation, the non resorptive fibers without oxidized cellulose are formed from a polymer chosen among poly(ethylene terephtalate) or some polyurethanes which are hydraulically stable, such as polymers obtained for example by reaction of a bischloroformate and a diamine or by reaction of diisocyanate with a dihydroxy component, or their copolymers.

In another variation, the non resorptive fibers without oxidized cellulose are formed from a polymer or a copolymer of the polyacetal type, e.g. containing patterns of polyoxymethylene.

What is claimed is:

1. A medical device intended to come into contact with a patient's tissue, the device comprising:
   a body having fibers provided without oxidized cellulose, the fibers without oxidized cellulose being non-resorptive, the body further including fibers containing oxidized cellulose, the fibers containing oxidized cellulose being resorptive, at least part of the fibers provided without oxidized cellulose being assembled with the fibers containing oxidized cellulose to form at least one composite thread, the composite thread being braided, woven or knitted, to form the body.

2. The device as recited in claim 1 wherein the body is a non-woven.

3. The device as recited in claim 2 wherein the fibers of the non-woven body are oriented in a preferred direction.

4. The device as recited in claim 1 wherein the fibers without oxidized cellulose are chosen from among synthetic polymers and natural polymers provided without oxidized cellulose.

5. The device as recited in claim 4 wherein the fibers without oxidized cellulose are formed from a polymer from at least one of the group consisting of: polyamides, polyolefins, halogenated polymers, poly(ethylene terephtalate), hydrolytically stable polyurethanes, polyethers, polysiloxanes, polyoxymethylenes, their copolymers and mixtures thereof.

6. The device as recited in claim 1 wherein the oxidized cellulose contained in the fibers containing oxidized cellulose is functionalized by a functional group, the oxidized cellulose advantageously includes a carboxyl group principally supported by the carbon 6 of the anhydroglucose unit, the carboxyl group being functionalized by the functional group.

7. The device as recited in claim 6 wherein the functional group is chosen from among a bioreactive agent.

8. The device as recited in claim 7 wherein the bioreactive agent is an anticoagulant, an antithrombogenic, an antimitotic, an anti-proliferation agent, an anti-adhesion agent, an anti-migration agent, a cell adhesion promoter, a growth factor, an anti-parasite molecule, an anti-inflammatory, an angiogenic, an angiogenesis inhibiter, a vitamin, a hormone, a protein, an antifungal, an antimicrobial molecule, an antiseptic, a cross-linking agent, or a contrast agent.

9. The device as recited in claim 1 wherein the body forms a tube or sheet, and/or the body delimits a liquid-tight wall.

10. The device as recited in claim 9 wherein the body is sealed against blood.

11. The device as recited in claim 1 wherein the device forms a prosthesis or a vascular endoprosthesis, a guided tissue regeneration membrane, a tube, a setting plate, a dialysis catheter, a perfusion catheter, a transfusion catheter, an artificial alimentation catheter, a transcutaneous implant, a lattice for tissue engineering, a micro and macro porous bone substitute, a dura mater substitute, a cell therapy matrix, a suture thread, a medical bandage or a vascular patch.

12. A method of manufacturing a medical device intended to come into contact with a patient's tissue, comprising the step of:
producing a body including fibers without oxidized cellulose, the fibers without oxidized cellulose being non resorptive, and fibers comprising oxidized cellulose, the fibers comprising oxidized cellulose being resorptive, the producing of the body including:
providing fibers without oxidized cellulose and fibers comprising cellulose intended to be oxidized;
forming the body from fibers provided without oxidized cellulose and cellulose fibers intended to be oxidized; and
selective oxidation of the cellulose fibers intended to be oxidized, after formation of the body to form the oxidized cellulose.

13. The method as recited in claim 12 further comprising, before the production of the body, assembly of at least one composite thread including fibers without oxidized cellulose and cellulose fibers intended to be oxidized, the producing step including braiding, knitting or weaving the composite thread to form the body.

14. The method as recited in claim 13 wherein the step of producing the body includes the provision of at least one first thread formed from fibers without oxidized cellulose and at least one second thread formed from cellulose fibers intended to be oxidized, then braiding, weaving or knitting the first thread with the second thread to form the body.

15. The method as recited in claim 12 wherein the fibers without oxidized cellulose are formed from at least one polymer from the group consisting of: polyamides, polyolefins, halogenated polymers, poly(ethylene terephtalate), hydrolytically stable polyurethanes, polyethers, polysiloxanes, polyoxymethylenes, their copolymers and mixtures thereof.

16. The method as recited in claim 12 further comprising, after a cellulose oxidation step, at least partial functionalization of the cellulose oxidized by a functional group.

* * * * *